United States Patent [19]
Herbig et al.

[11] Patent Number: 5,798,119
[45] Date of Patent: Aug. 25, 1998

[54] OSMOTIC-DELIVERY DEVICES HAVING VAPOR-PERMEABLE COATINGS

[75] Inventors: Scott M. Herbig, Deschutes, Oreg.; Eric J. Miller, Mount Pleasant, Wis.

[73] Assignee: S. C. Johnson & Son, Inc., Racine, Wis.

[21] Appl. No.: 489,888

[22] Filed: Jun. 13, 1995

[51] Int. Cl.$^6$ .............. A61K 9/22; A61K 9/24; A61K 9/32; A61K 9/34
[52] U.S. Cl. .............. 424/473; 424/472; 604/890.1; 604/892.1
[58] Field of Search .............. 424/473, 457, 424/463, 468, 472, 476, 480, 482, 408, 409; 604/890.1, 892.1

[56] References Cited

U.S. PATENT DOCUMENTS

| | | | |
|---|---|---|---|
| 3,247,066 | 4/1966 | Milosovich, Jr. | 167/82 |
| 3,760,804 | 9/1973 | Higuchi et al. | 128/260 |
| 3,760,805 | 9/1973 | Higuchi et al. | 128/260 |
| 3,770,199 | 11/1973 | Hoek et al. | 239/54 |
| 3,845,770 | 11/1974 | Theeuwes et al. | 424/15 |
| 3,952,741 | 4/1976 | Baker | 128/260 |
| 3,995,631 | 12/1976 | Higuchi et al. | 128/260 |
| 4,002,458 | 1/1977 | Hofacker | 71/27 |
| 4,016,880 | 4/1977 | Theeuwes et al. | 128/260 |
| 4,111,201 | 9/1978 | Theeuwes | 128/260 |
| 4,111,202 | 9/1978 | Theeuwes | 128/260 |
| 4,177,256 | 12/1979 | Michaels et al. | 424/22 |
| 4,340,054 | 7/1982 | Michaels | 128/260 |
| 4,356,696 | 11/1982 | Mason | 60/606 |
| 4,356,969 | 11/1982 | Obermayer et al. | 239/60 |
| 4,605,165 | 8/1986 | VanLoveren et al. | 239/6 |
| 4,685,918 | 8/1987 | Amidon et al. | 604/892 |
| 4,756,844 | 7/1988 | Walles et al. | 252/95 |
| 4,781,714 | 11/1988 | Eckenhoff et al. | 604/890.1 |
| 4,871,542 | 10/1989 | Vilhardt | 424/423 |
| 4,915,301 | 4/1990 | Munteanu | 239/45 |
| 4,940,465 | 7/1990 | Theeuwes et al. | 604/892.1 |
| 4,968,507 | 11/1990 | Zentner et al. | 424/465 |
| 5,221,278 | 6/1993 | Linkwitz et al. | 604/890.1 |

FOREIGN PATENT DOCUMENTS

| | | |
|---|---|---|
| 0 357 369 | 8/1989 | European Pat. Off. |
| WO 92/05775 | 9/1990 | WIPO . |
| WO 93/06819 | 10/1991 | WIPO . |
| WO 94/23765 | 4/1993 | WIPO . |
| WO 95/03033 | 2/1995 | WIPO . |

OTHER PUBLICATIONS

Article: "Controlled Release of Biologically Active Agents," [1987]132–133 by R.W. Baker.

Article: "Controlled Release" in Membrane Handbook, by W.S.W. Ho K.K. & Sirkar, K.K., Editors|1992|pp. 915–935.

(List continued on next page.)

*Primary Examiner*—Thurman K. Page
*Assistant Examiner*—James M. Spear

[57] ABSTRACT

An osmotic device that, following the imbibition water vapor, provides for the controlled release of a beneficial agent to a non-aqueous environment. The device comprises a hydrophilic formulation and a beneficial agent, surrounded by a wall. The wall is formed at least in part of a semipermeable hydrophobic microporous membrane having an average pores size between about 0.1 μm and 30 μm. The pores are substantially filled with a gas phase. The hydrophobic membrane is permeable to water in the vapor phase and the hydrophobic membrane is impermeable to an aqueous medium at a pressure less than about 100 Pa. The beneficial agent is released, for example, by osmotic pumping or osmotic bursting upon imbibition of sufficient water vapor into the hydrophilic formulation. The high water fluxes attendant with these vapor-permeable hydrophobic membranes facilitate the delivery of large quantities of beneficial agents without requiring large surface areas (quantities) of hydrophobic microporous membrane. In addition, use of vapor-permeable hydrophobic microporous membranes allow osmotic devices to be used in environments having limited water availability, such as air or soil.

42 Claims, 3 Drawing Sheets

OTHER PUBLICATIONS

Article "Osmotic Delivery of Peptides and Macromolecules," Ad.Drug.Del.Rev.,4|1990|225-276 by A. Amkraut, J.B. Eckenhoff & K. Nichols.

Thesis: "An Experimental Study of Osmotic Pumping by Highly Microporous Polymer Membranes," by B.C. Batt, Univ. of Kansas 1982.

Article: "An In Vitro Drug Release Rate Method for Lipoidal Materials", by A.E. Merfeld, J.L. Haslam & G.S. Rock, Inter.Journal of Pharm., 69:1(1991)63–67.

Literature: "Controlled Release of Drugs with Microporous Polymers" by H.E. Junginger & J. Verhoven, Proceedings of 11th International Symposium on Controlled Rel. of Bioactive Mat'l, Controlled Release Society, Lincolnshire, IL (1984).

Article: Controlled Long–Term Release of Small Peptide Hormones Using a New Microporous Polypropylene Polymer: Its Application for Vasopressin in the Brattleboro Rat & Potential Perinatal Use by J. Kruisbrink & G.J. Boer, Netherlands Institute for Brain Research, Amsterdam, in J. Pharm. Sci.73:12(1984)/1713–1718.

OSMOTIC-DELIVERY DEVICES HAVING VAPOR-PERMEABLE COATINGS

BACKGROUND OF THE INVENTION

Osmotic-delivery systems typically operate by imbibing water through a membrane into a core that contains an osmotically active agent (osmagent) and a beneficial agent; the imbibed water causes an increase in hydrostatic pressure within the core, and the beneficial agent is then released by being pumped out through a delivery port or by rupture of the membrane. Osmotic devices based on semipermeable coatings have been described in the literature and have been produced commercially for several years (see, for example, Baker, R. W., *Controlled Release of Biologically Active Agents*, [1987] 132–133; Smith, K. L., and S. M. Herbig, "Controlled Release," in *Membrane Handbook*, W. S. W. Ho K. K. and Sirkar, K. K., eds., [1992] 915–935). The beneficial agent is typically released into the aqueous solution in which the device is placed, although, as described in the literature, a catheter can be connected to the osmotic device so that the beneficial agent can be delivered to an aqueous environment remote from the site of the device (Amkraut, A., J. B. Eckenhoff, and K. Nichols, "Osmotic Delivery of Peptides and Macromolecules," *Ad. Drug. Del. Rev.*, 4[1990]255–276; Cuevas, P., A. M. Gonzales, F. Carceller, and A. Baird, *Circ. Res.*, 69[1991]360–369). Osmotic-delivery systems have been developed that release the beneficial agent either in a sustained manner via osmotic pumping or as a bolus via osmotic bursting (e.g., U.S. Pat. Nos. 3,247,066, 3,952,741B1, 4,016,880, and 4,177,256). These delivery systems rely on semipermeable coatings to control the influx of water and to contain the beneficial agent within the core until it is released.

Generally, semipermeable coatings are either dense, microporous, or asymmetric in structure (e.g., U.S. Pat. Nos. 3,845,770, 4,968,507, and European Patent Application 89308716.3, Publication No. 0357369). In addition, typically the semipermeable membranes must be wetted by an aqueous solution to allow for release of the beneficial agent (Batt, B. C., "An Experimental Study of Osmotic Pumping by Highly Microporous Polymer Membranes," M. S. thesis, University of Kansas, 1982; U.S. Pat. Nos. 4,968,507 and 4,340,054). Also, at least one delivery port must be formed in the semipermeable coating (e.g., by drilling or by forming pores in the coatings) for sustained delivery of a beneficial agent. Alternatively, the beneficial agent can be released by bursting the coating as a result of hydrostatic pressure generated in the core by osmosis.

Osmotic devices have been described that have a combination of a hydrophilic semipermeable membrane covering a portion of the device and a hydrophobic porous membrane covering another portion of the device. In this case, the pores (typically <100 µm in diameter) of the hydrophobic-porous-membrane portion of the device contain hydrophobic liquids (e.g., oils), which inherently wet the hydrophobic membrane and are entrained therein. Water is imbibed through the hydrophilic semipermeable membrane into the device, and the resultant hydrostatic pressure forces the oils out through the hydrophobic membrane pores. Thus, these devices facilitate the osmotic delivery of oils or beneficial agents that can be dissolved in oils. Such devices are described in Merfeld, A. E., J. L. Haslam, and G. S. Rork, "An In Vitro Release Method for Lipoidal Materials," *Inter. Journal of Pharm.*, 69:1(1991)63–67, U.S. Pat. No. 4,685,918; and International Application WO 92/05775.

Early osmotic devices disclosed separating the osmagent from the beneficial agent (U.S. Pat. Nos. 3,995,631 and 4,340,054). Subsequently, osmotic devices have been disclosed that describe having the osmagent in one layer and the beneficial agent in an adjacent layer (U.S. Pat. Nos. 4,111,201 and 4,111,202). These devices utilize semipermeable coatings that are wetted by water and describe delivering the beneficial agent to the surrounding fluid.

Osmotic devices for lodgment in an aqueous environment in the interior of an animal have been described that utilize porous hydrophobic material to allow water inhibition while retaining non-volatile materials within the core (International Publication No. WO 93/06819). The use of porous hydrophobic material as the semipermeable membrane in osmotic devices has also been disclosed that use porous hydrophobic membranes for use in an aqueous environment (U.S. patent application Ser. No. 08/096,144), now abandoned. Thus, although the use of porous hydrophobic materials has been disclosed, their use in non-aqueous environments has not been contemplated.

Diffusional (i.e., non-osmotic) release of beneficial agents through pores in hydrophobic "nonsemipermeable" coatings has also been described in the literature (e.g., Junginger, H. E., and J. Verhoven, "Controlled Release of Drugs with Microporous Polymers," *Proceedings of the 11th International Symposium on Controlled Release of Bioactive Materials*, Controlled Release Society, Lincolnshire, Ill. (1984)4–5; Kruisbrink, J., and G. J. Boer, *J. Pharm. Sci.*, 73:12(1984)1713–1718; and U.S. Pat. Nos. 4,871,542, 4,756,844, and 4,002,458). Generally to deliver the beneficial agent to aqueous solutions, these coatings have large pores (e.g., >100 µm). In general, the beneficial agent (or solution containing beneficial agent) must wet the pores of the coating. The large pores facilitate wetting of the pores by an aqueous beneficial-agent-containing solution. Hydrophobic microporous films have also been used to release beneficial agents to non-aqueous environments at a controlled rate (U.S. Pat. Nos. 3,770,199, 4,356,696, 4,915,301, and 4,605,165). Release from these devices is also by diffusion of the beneficial agent through the pores in the film.

In another field of art, the field of chemical separations, hydrophobic microporous membranes are used in gas-transport/liquid-barrier applications. They have been used to selectively transport vapors and to act as barriers to liquids. Examples of such use are blood oxygenators, membrane-distillation processes, and breathable waterproof fabrics. Vapor-permeable coatings have also been used as selective and/or protective coatings on sensors or sorbents. Sensor devices used to detect gases are commonly coated with a hydrophobic microporous film to prevent the electrode from becoming wetted. In addition, ion-exchange resins have been coated with vapor-permeable coatings for the selective removal of ammonia. Methods to make vapor-permeable membranes and their application are described in several references (e.g., Kesting, R. E., "Synthetic Polymer Membranes," 1985).

The controlled release of beneficial agents to non-aqueous environment has been accomplished using many technologies. As discussed earlier, microporous films have been used to control the rate of delivery (by diffusion) to non-aqueous environments. Release from such systems occurs by the beneficial agent wetting the pores and diffusing to the surface or diffusing through the pores in the vapor state. The release of beneficial agents such as air fresheners from osmotic systems has been disclosed (U.S. Pat. Nos., 4,940, 465 and 4,781,714 and International patent application WO 94/23765) using semipermeable membranes to facilitate osmotic imbibition of water into the devices. The semipermeable membranes described typically have low water permeability and thus require large surface area to achieve the desired flux and can also require long times before the membrane becomes wetted and consequently allows osmotic imbibition. Combination of an osmotic device that uses a vapor-permeable membrane and delivers the beneficial agent to a non-aqueous environment has not been previously disclosed.

Although the above-described devices make a significant advance in the field of delivery devices there is a continuing search for alternative delivery devices.

SUMMARY OF INVENTION

This invention is directed to an osmotic device that, following the imbibition of water vapor, provides for the controlled release of a beneficial agent to a non-aqueous environment. The device comprises a hydrophilic formulation containing an osmagent and a beneficial agent, surrounded by a container wall. The wall of the container adjacent to the hydrophilic formulation is formed at least in part of a semipermeable hydrophobic membrane having an average pore size between about 0.1 µm and 30 µm. The pores are substantially filled with a gas phase. The hydrophobic membrane is permeable to water in the vapor phase and the hydrophobic membrane is impermeable to an aqueous medium at a pressure less than about 100 Pa. The wall of the container adjacent to the beneficial agent has at least one opening that allows the beneficial agent to be released. In operation the device is placed in water or in an aqueous solution such that the semipermeable hydrophobic membrane is immersed and the opening for release of the beneficial agent is not immersed. The beneficial agent is released, for example, by osmotic pumping or osmotic bursting upon imbibition of sufficient water vapor into the device core creating a hydrostatic pressure that forces the beneficial agent out of the device.

A flexible or movable barrier layer may be placed between the beneficial agent and the hydrophilic formulation to prevent mixing. This flexible or movable layer will also prevent contact between the water imbibed into the hydrophilic formulation and the beneficial agent. In addition, water may be contained in the device, eliminating the need for an external water source. In this case, water would be contained in a sealed compartment adjacent to the semipermeable hydrophobic membrane. To initiate operation of the device, the seal between the water compartment and the semipermeable hydrophobic membrane would be broken, allowing water vapor to be imbibed through the hydrophobic membrane into the hydrophilic formulation.

These devices have the advantage of high water-imbibition rates attendant with these vapor-permeable membranes, which facilitates high release rates of beneficial agent. In addition, hydrophobic microporous materials are compatible with common inexpensive container materials, allowing for ease in assembly and in forming seals with the container. Since the hydrophobic microporous material is selective only for water vapor, the hydrophilic formulation within the device will remain contained within the device.

DETAILED DESCRIPTION OF THE INVENTION

Figure 1:
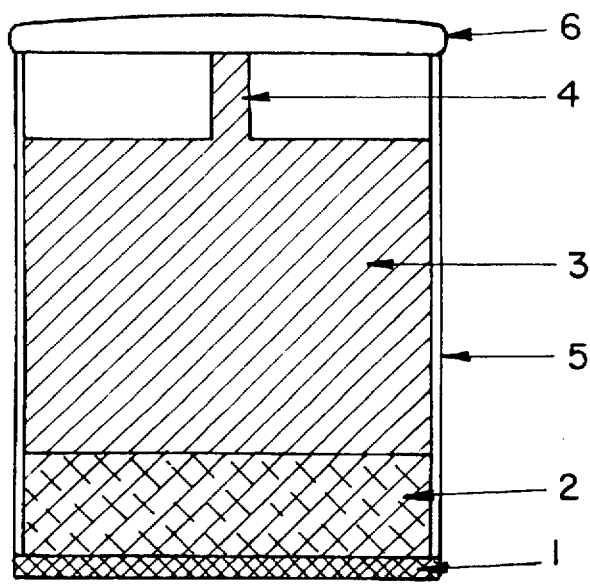
FIG. 1 is a diagram of an exemplary device of this invention where the hydrophilic formulation and beneficial agent are in adjacent layers.

The devices of this invention operate by imbibing water into the device through a microporous hydrophobic semi-permeable membrane. This imbibition of water creates a hydrostatic pressure within the device causing the beneficial agent to be pumped out of the device into a non-aqueous environment. By non-aqueous environment, we mean that the beneficial agent would be released into an environment that does not consist of liquid water and is not any cavity or portion of animals or man. Water for imbibition must be provided in an external reservoir or included in a separate compartment within the device. Water in an external reservoir (e.g., open water or water in an open container such as a cup, bowl, or vase) could be utilized by placing the device in the water such that the hydrophobic membrane is immersed in the water and the opening for delivery of beneficial agent is out of the water. For example, devices similar to those shown in FIGS. 1, 2, and 3 could sit in water such that the hydrophobic membrane was toward the bottom of the container and the emanator pad is out of the water. In such a device, imbibition of water could be used to pump fragrance out onto the emanator pad, providing constant release of the fragrance mixture, which then evaporates from the emanator pad into the air. Water reservoirs could also be moist soil, or bodies of water such as a stream, river, pond, lake, or ocean. In each case, the device must be positioned so that the hydrophobic membrane is immersed in the water reservoir and the delivery port for beneficial agent is out of the water reservoir and in a non-aqueous environment. Water reservoirs could also be moisture in the air. The hydrophilic formulation could imbibe water from the air through microporous hydrophobic materials to generate the pressure necessary to osmotically pump beneficial agent out of the device.

Water could also be contained within a sealed compartment of the device. To operate in this manner, a seal between the water compartment and the hydrophobic membrane must be ruptured or otherwise caused to open. This could be accomplished, for example, by puncturing or ripping the seal. Water would then be imbibed from the water reservoir through the hydrophobic membrane into the hydrophilic formulation. As described above, this imbibition of water would force the beneficial agent out of the delivery opening into a non-aqueous environment.

Typically, in the devices of this invention, water vapor is imbibed into the hydrophilic formulation from the aqueous solution through the pores in the membrane due to osmosis (liquid water is excluded by the hydrophobicity of the membrane; liquid water will not wet the pores of the membrane). Due to water-vapor imbibition, a hydrostatic pressure is developed within the compartment containing the hydrophilic formulation. The hydrostatic pressure in this compartment causes the beneficial agent to be released through the opening to the environment of use in a sustained manner by an osmotic-pumping mechanism. Alternatively, for example, the hydrostatic pressure can cause the outlet for the beneficial agent to burst open, releasing the beneficial agent.

Any semipermeable hydrophobic microporous membrane (membrane means) that is solid under the conditions of use, is permeable to water vapor, and the pores of which are substantially filled with a gas phase and are not wetted by the aqueous medium in contact with the semipermeable hydrophobic membrane may be used in this invention. By aqueous medium is meant a composition containing water as an available liquid component (e.g., solutions of organic or inorganic substances particularly electrolytes, and mixtures of substances in water, e.g., moist soil). By substantially filled with a gas phase is meant that most of the pores do not contain solids or liquids that block the pores, but contain gases such as air, oxygen, nitrogen, or water vapor. Typically the hydrophobic membrane has pores having an average pore size between about 0.1 μm and 30 μm preferably less than 10 μm and the hydrophobic membrane is impermeable to water at a pressure less than about 100 Pa, and preferably less than 100,000 Pa.

Preferably, the hydrophobic membrane has a water-vapor transmission rate greater than 2 g-mm/m$^2$-24 hour, a contact angle with water greater than 50 degrees, and a total pore volume of between 5% and 95%. Preferably, the membrane material itself (in the nonporous state) is substantially impermeable to the hydrophilic formulation (i.e., the hydrophilic formulation will not diffuse through the membrane material to an appreciable extent). By substantially impermeable is meant less than 1% of the formulation is released through the membrane material over a 24-hour period. In addition, preferably the membrane material (in the nonporous state) has an intrinsic permeability to water of less than $1 \times 10^{-7}$ cm$^3$(STP)-cm/cm$^2$-sec-cmHg. Although the membrane thickness may be any dimension that provides appropriate water inhibition and structural stability, the membrane is preferably 5 μm to 2 cm in thickness. The pores in the membrane must create at least one continuous pathway through the membrane thickness.

Typically, the membrane may be combined with another type of impermeable wall portion to totally surround the hydrophilic formulation and beneficial agent. Preferably the membrane is polymeric or a wax, although appropriately treated inorganic materials such as ceramics, metals, or glasses may be used.

The following is a preferred listing of materials that can be used to make the hydrophobic membrane of this invention. The polymer's molecular weight should be of such a size that the polymer is solid at the temperature of use and appropriate for the application (e.g., durable for handling purposes).

Polysulfones, polyethersulfones, polytetrafluoroethylene, polyvinyl chloride, polyacrylonitrile, polyvinylidene chloride, polyvinylidene fluoride, polyimides, polycarbonates, polyurethanes, polyvinyl acetates, polyamides, polysiloxanes, polyesters.

Polyalkenes such as polyethylene, ethylene vinyl alcohol copolymer, polypropylene, poly(1,2-dimethyl-1-butenylene), poly(1-bromo-1-butenylene), poly(1,butene), poly(1-chloro-1-butenylene), poly(1-decyl-1-butenylene), poly(1-hexane), poly(1-isopropyl-1-butenylene), poly(1-pentene), poly(3-vinylpyrene), poly(4-methoxy-1-butenylene); poly(ethylene-co-methyl styrene), polyvinyl chloride, poly(ethylene-cotetrafluoroethylene), poly (ethylene-terephthalate), poly (dodecafluorobutoxylethylene), poly(hexafluoroprolylene), poly(hexyloxyethylene), poly(isobutene), poly(isobutene-coisoprene), poly(isoprene), poly-butadiene, poly[(pentafluoroethyl)ethylene], poly[2-ethylhexyloxy) ethylene], poly(butylethylene), poly(tertbutylethylene), poly(cyclo-hexylethylene), poly[(cyclohexylmethyl)ethylene], poly(cyclopentyl-ethylene), poly(decylethylene), poly(dodecylethylene), poly(neopentylethylene), poly(propylethylene).

Polystyrenes such as poly(2,4-dimethyl styrene), poly(3-methyl styrene), poly(4-methoxystyrene), poly(4-methoxystyrene-stat-styrene), poly(4-methyl styrene), poly(isopentyl styrene), poly(isopropyl styrene).

Polyvinyl esters or polyvinyl ethers such as poly(benzoylethylene), poly(butoxyethylene), poly(chloroprene), poly(cyclohexyloxyethylene), poly(decyloxyethylene), poly(dichloroethylene), poly(difluoroethylene), poly(vinyl acetate), poly(vinyltrimethylstyrene).

Polyacrylic acid derivatives such as polyacrylates, polymethyl methacrylate, polyethyl methacrylate, poly(acrylic acid) higher alkyl esters, poly(hexadecyl methacrylate-co-methylmethacrylate), poly(methylacrylate-co-styrene), poly(n-butyl methacrylate), poly(n-butyl-acrylate), poly(cyclododecylacrylate), poly(benzylacrylate), poly(butylacrylate), poly(secbutylacrylate), poly(hexyl acrylate), poly(octylacrylate), poly(decylacrylate), poly(dodecylacrylate), poly(2-methyl-butylacrylate), poly(adamantyl methacrylate), poly(benzyl methacrylate), poly(butyl methacrylate), poly(2-ethylhexyl methacrylate), poly(octyl methacrylate), acrylic resins.

Polyethers such as poly(octyloxyethylene), poly(oxyphenylethylene), poly(oxypropylene), poly(pentyloxyethylene), poly(phenoxy styrene), poly(secbutoxylethylene), poly(tert-butoxyethylene).

Exemplary natural and synthetic waxes useful as the hydrophobic membrane include: insect and animal waxes such as Chinese insect wax, spermaceti, fats and wool wax; vegetable waxes such as bamboo leaf wax, candelilla wax, carnauba wax, Japan wax, ouricury wax, Jojoba wax, bayberry wax, Douglas-fir wax, cotton wax, cranberry wax, capeberry wax, rice-bran wax, castor wax, Indian corn wax, hydrogenated vegetable oils (e.g., castor, palm, cottonseed, soybean), sorghum grain wax, Madagascar wax, orange peel wax, shellac wax, sisal hemp wax, and rice wax; mineral waxes such as Montan wax, peat waxes, petroleum wax, petroleum ceresin, ozokerite wax, microcrystalline wax, and paraffins; and synthetic waxes such as polyethylene wax, Fischer-Tropsch wax, chemically modified hydrocarbon waxes and cetyl esters wax.

Especially preferred membrane materials include polyethylene, polypropylene, polyvinylidene fluoride, polytetrafluoroethylene, and polyvinyl chloride.

The semipermeable hydrophobic membrane covers at least a portion of the hydrophilic formulation which must contain an osmagent. The osmagent may be any material that causes the osmotic pressure of the hydrophilic formulation to be greater than that of the aqueous medium. The hydrophilic formulation must have an effective osmotic pressure greater than that of the surrounding aqueous medium so that there is a net driving force for water vapor to enter the device. The higher osmotic pressure within the hydrophilic formulation allows the hydrostatic pressure in the device to increase to achieve either the desired osmotic pumping or bursting causing release of the beneficial agent. The osmagent can be either soluble or swellable. Examples of osmotically effective solutes are inorganic and organic salts and sugars. Osmotically effective compounds may be used singly or in combination and include, for example, magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, water soluble acids, alcohols, surfactants, and carbohydrates such as sugars (e.g., raffinose, sucrose, glucose, lactose, fructose), sugar derivatives, algin, sodium alginate, potassium alginate, carrageenan, fucoridan, furcellaran, laminaran, hypnea, gum arabic, gum ghatti, gum karaya, locust bean gum, pectin, and starch.

Typically for those devices that function by osmotic bursting, a water-swellable component such as a hydrogel is used. The swellable excipient aids in forcing open a delivery port for release of beneficial agent as a result of the imbibition of water vapor into the device. Exemplary hydrogels include polyacrylic acid derivatives (e.g., polyacrylates, poly(acrylic acid) higher alkyl esters, polyacrylamides, poly (hydroxy ethyl methacrylate), poly(vinyl alcohol), poly (ethylene oxide), poly(N-vinyl-2-pyrrolidone), naturally occurring resins such as polysaccharides (e.g., dextrans, water-soluble gums, starches, and chemically modified starches), cellulose derivatives (e.g., cellulose esters, cellulose ethers, chemically modified cellulose, microcrystalline cellulose, sodium carboxymethylcellulose, and methylcellulose).

Preferred hydrogels include ethylene oxide derivatives such as polyethylene oxide (PEO), because of its relatively large capacity to absorb water and swell, its availability in a variety of different molecular weights in commercial quantities, its biocompatibility, and its safety and favorable toxicity properties. PEO is commercially available and can be obtained in a variety of different molecular weights. Other preferred hydrogels are starches, gums, crosslinked hydrogels, and carboxymethylcellulose.

The hydrogel employed can be a blend of, for example, two or more polymers. For example, different hydrogels comprising blends of PEO polymers of different molecular weights can be prepared and employed. Such blends can be adjusted to assist in achieving the desired delivery rates for the beneficial agents.

The beneficial agents used in the devices of this invention include for example, any active substance that produces a desired effect in the non-aqueous environment of use.

Examples of active substances include inorganic and organic compounds such as agrichemicals, including insecticides, herbicides, fertilizers, fungicides, pheromones, algaecides, insect growth regulators, and plant growth regulators; reaction catalysts; reaction feedstocks; pH-controlling agents; enzymes, enzyme inhibitors; disinfectants; odor absorbants; flavors; and fragrances.

The release profile can be tailored so that the release duration is from instantaneous (i.e., bursting) to longer than several months. For example, a device containing a hydrophilic formulation with a water-swellable hydrogel designed to expand and burst open a film containing the beneficial agent has a very short release duration-essentially as fast as the beneficial agent could evaporate or otherwise disperse. A device in which the beneficial agent is released by osmotic pumping can have a much longer release duration. In addition, release of beneficial agent can be initiated by bursting open a constrained opening, and then release could continue over a long time by osmotic pumping.

The release profile of the devices of this invention can also be advantageously tailored by altering time lags between exposure of the device to the aqueous solution and release of the beneficial agent. Thus, preferably the membrane pores, membrane composition, and membrane thickness are of a number, composition, and size sufficient to provide the desired time lag.

Preferred devices include those schematically shown in FIGS. 1-5, and described generally below. Particularly preferred devices include those having a hydrophobic semipermeable membrane of polyethylene, polypropylene, or polyvinylidene fluoride. It is especially preferred that the hydrophilic formulation contains an osmagent that is a sugar or a salt. Particularly preferred is when the hydrophilic formulation has a surface tension of about 60–70 dyn/cm.

The shape and dimensions of the dispensing device can vary based on the particular application. The device may be formed in a shape that is aesthetically pleasing. It is especially preferred that the device resemble a flower or natural plant for releasing a fragrance. The dispensing-device dimensions may also vary with the quantity of beneficial agent that must be delivered. Preferably, for devices that release fragrances to freshen the air, the device will contain 0.1 to 400 grams of fragrance and 1 to 100 grams of hydrophilic formulation. For other applications, such as agrichemicals, chemical reactions, flavors, and fragrances, shapes and sizes will be determined by the method of use and may be different from those listed above.

A clearer understanding of the devices of this invention may be had by reference to FIGS. 1-5. In FIG. 1, the beneficial agent 3 and the hydrophilic formulation 2 are formed in layers inside a container made of walls that are impermeable to both the beneficial agent 3 and the hydrophilic formulation 2. The hydrophilic formulation 2 is next to the porous hydrophobic semipermeable membrane 1. In operation, the device is placed in water so that the hydrophobic membrane 1 is immersed in water and the delivery port 4 and emanator pad 6 are out of the water and exposed to the non-aqueous environment. Water is imbibed into the hydrophilic formulation 2 through the hydrophobic membrane 1. The increase in volume due to water imbibition creates a hydrostatic pressure that forces the beneficial agent 3 out of the delivery port 4 and onto the emanator pad 6, where it is available to the desired environment.

Figure 2:
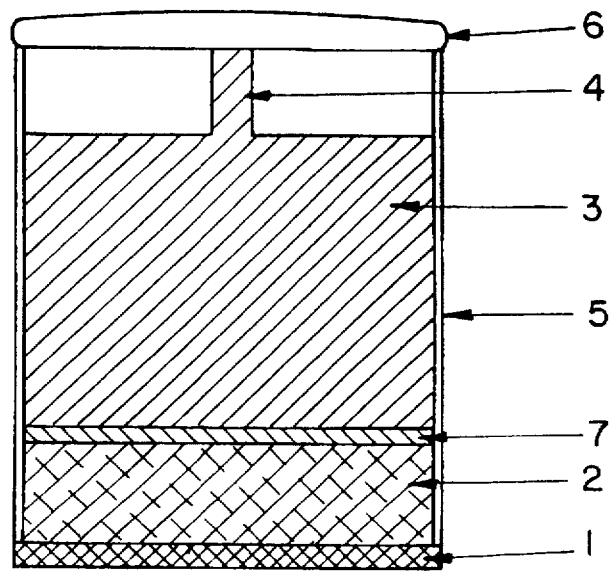
FIG. 2 is a diagram of an exemplary device of this invention where the hydrophobic formulation and the beneficial agent are separated by a movable piston-like barrier.

The device shown in FIG. 2 is similar to the device in FIG. 1 with the addition of a movable piston-like barrier 7 between the hydrophilic formulation 2 and the beneficial agent 3. As water is imbibed into the hydrophilic formulation, the hydrostatic pressure created forces the movable barrier 7 toward the delivery port 4 and forces the beneficial agent 3 out the delivery port 4. The movable barrier prevents contact between the hydrophilic formulation and beneficial agent.

Figure 3:
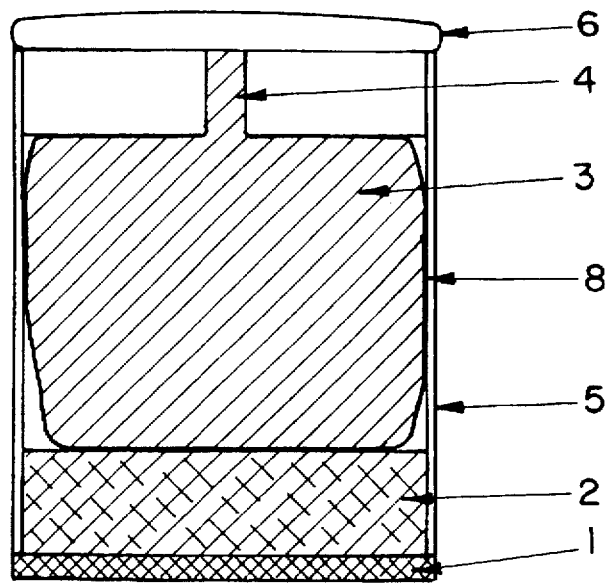
FIG. 3 is a diagram of an exemplary device of this invention where the hydrophilic formulation and the beneficial agent are separated by a flexible barrier.

The device in FIG. 3 is similar to the device in FIG. 2 except that the movable piston-like barrier 7 has been replaced with a flexible barrier film 8. This flexible barrier film 8 collapses as water is imbibed into the hydrophilic formulation 2, which causes the beneficial agent 3 to be delivered.

Figure 4:
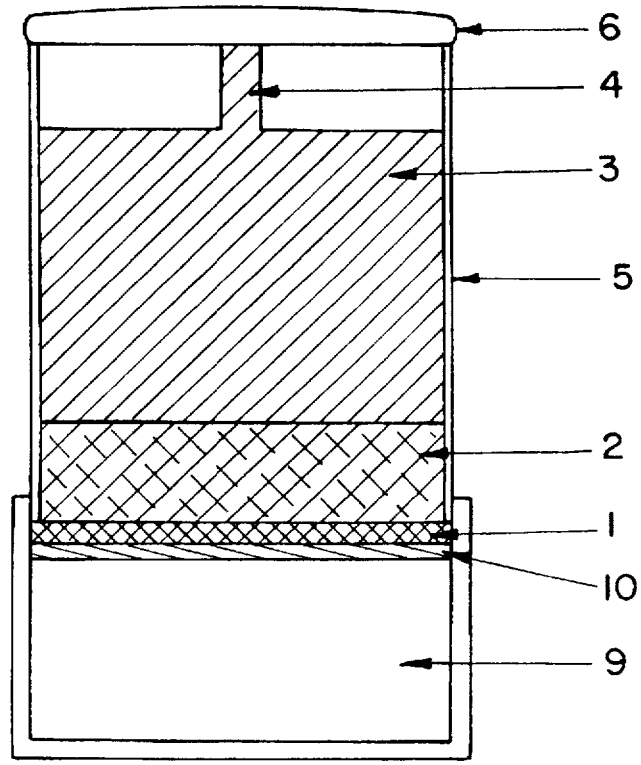
FIG. 4 is a diagram of an exemplary device of this invention where the hydrophilic formulation and the beneficial agent are in adjacent layers and a water reservoir with a breakable seal is included in the device.

FIG. 4 is similar to FIG. 1 with the addition of a water reservoir 9 within the device. Similarly, a water reservoir could be added to the devices shown in FIGS. 2 and 3. Based on the device design only a small quantity of water is required to displace a large quantity of beneficial agent. For example, by using a movable piston, the hydrophilic formulation could be in a small tube that moves a larger-diameter piston that pumps out beneficial agent. To provide storage stability, a breakable seal 10 is placed between the water reservoir 9 and the porous hydrophobic semipermeable membrane 1. This prevents water imbibition into the hydrophilic formulation during storage. To initiate operation of the device, the breakable seal 10 must be ruptured or opened. This could be accomplished in a number of ways, such as by twisting the device and ripping the seal or by puncturing the seal. Once the seal is ruptured, water can then be imbibed into the hydrophilic formulation, causing release of the beneficial agents.

Figure 5:
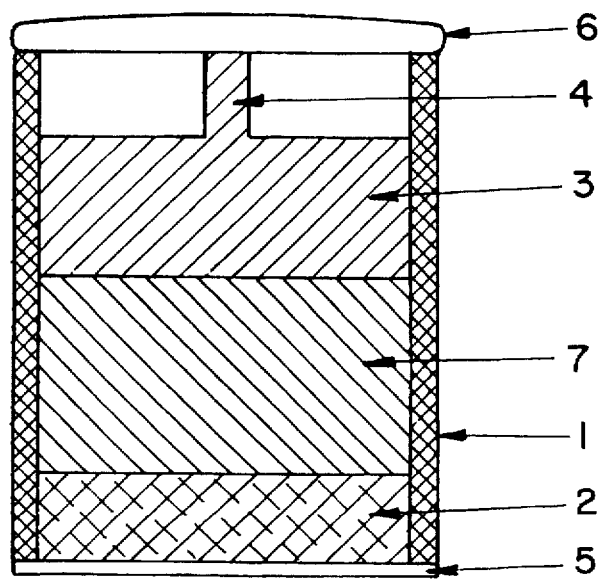
FIG. 5 is a diagram of an exemplary device of this invention where the hydrophobic microporous material is in the form of a tube and a movable piston separates the hydrophilic formulation and the beneficial agent.

To release beneficial agent at a higher rate at later times, a device as shown in FIG. 5 could be made. In FIG. 5, the hydrophobic microporous material is formed as a tube 1. As water is osmotically imbibed into the hydrophilic formulation 2, the movable piston 7 is forced up pumping the beneficial agent 3 to the emanator pad 6. As the movable piston is forced up, the surface area of the hydrophobic microporous material 1 increases. The water flux increases proportionally to the increase in surface area. Thus, as beneficial agent is released, the rate of release increases due to increased surface area of the hydrophobic microporous material.

The rate of release of beneficial agent from these devices is governed mostly by the surface area, thickness, and porosity of the hydrophobic microporous semipermeable membrane and the osmotic driving force across the hydrophobic membrane. The osmotic driving force is the difference in osmotic pressure between the hydrophilic formulation and the water reservoir. As the osmotic driving force increases, the water imbibition rate increases proportionately. Thus, hydrophilic formulations that contain osmagents with higher osmotic pressures will have higher water-imbibition rates and consequently higher release rates.

Flux of water through the porous hydrophobic membrane is proportional to the porosity and inversely proportional to the thickness of the material. The greater the porosity, the easier the water vapor can move through the membrane. Thus, water flux increases as porosity increases. As material thickness is made thinner the water vapor has a shorter distance to move through the pores and consequently the water flux increases. Thus, to increase water flux and, consequently, release rates, one would use a material with increased porosity and/or decreased thickness.

Likewise, the water flux through the hydrophobic membrane is proportional to the surface area of membrane. Thus, the rate of release can be controlled by controlling the surface area. A device could be made such that an opening exposing the hydrophobic membrane to water could be closed or opened to varying degrees to allow adjustment of the release rate during use. The opening could be formed in the seal between the water reservoir and the hydrophobic membrane, which in the closed position would provide the barrier desired for storage and then could be opened to the desired degree allowing the release rate to be controlled during use. The rate of release could be either increased or decreased with time by having the surface area change.

The devices of this invention may be made using the above-described materials using the following processes and other conventional methods.

Microporous coatings can be made by a variety of methods, such as phase inversion, scintering, leaching, and irradiation. All of these methods for forming hydrophobic micropores films have been described in the literature, especially for use as membranes for separations (*Synthetic Polymer Membranes*, by R. E. Kesting, John Wiley & Sons, 1985). Several different phase-inversion methods, such as the vapor-quench process, the dry process, the liquid-quench process, and the thermal process, can be used to form microporous coatings. Commercially available microporous films or microporous hollow fibers or tubes or other geometries can be used in this invention and can be used as part of the container.

In the vapor-quench process, membrane formation is accomplished by penetration of a precipitant for the polymer into the solution film from the vapor phase, which may be saturated with the solvent used. A porous membrane is produced without a skin and with an even distribution of pores over the membrane thickness.

In the dry process, the polymer is dissolved in a mixture of a solvent and a poor solvent, of which the solvent is more volatile. The polymer precipitates when the mixture shifts in composition during evaporation to a higher nonsolvent content. A skinned or nonskinned microporous membrane can be the result.

In the liquid-quench process, film formation is caused by the immersion of a film or coating or polymer solution into a nonsolvent bath. The polymer precipitates as a result of solvent loss and nonsolvent penetration (exchange of the solvent with nonsolvent). A skinned or nonskinned membrane can be the result.

In the thermal process, a solution of polymer in a latent solvent is brought to phase separation by a cooling step. When evaporation of the solvent is prevented, the membrane typically will be porous.

Microporous coatings can also be made by inclusion of a leachable component in the coating formulation. For example, small particles of sugar, salt, or water-soluble materials equal to the desired pore size can be suspended or dissolved in the coating solution. Once the coating is applied, the water-soluble materials can be leached out by immersion in water, forming a microporous structure. Alternatively, the small particles can consist of volatile solids such as menthol, naphthalene, camphor, phenol, ammonium acetate, or ammonium carbonate.

Microporous hydrophobic films have also been made by scintering particles of hydrophobic polymers or ceramic or metals together under heat and pressure. Microporous hydrophobic films are also commonly made by irradiation. Films can be cured (precipitated) by irradiation, forming a microporous structure. In addition, pores can be formed in dense films by a nucleation track-etched method.

Porous hydrophobic membranes/materials are readily available from a number of suppliers. For example, flat films and sheets are available from AKZO (Wuppertal, Germany); Hoechst Celanese (Charlotte, N.C.); Millipore (Befford, Mass.); and W. L. Gore & Associates, Inc. (Elkton, Md.). Scintered porous hydrophobic materials are available from companies such as Purex (Fairburn, Ga.), and Interflow Technologies (Brooklyn, N.Y.). In addition, porous hydrophobic hollow fibers and tubes are available from companies such as AKZO, Hoechst Celanese, and AquaAir, Inc. (Bend, Oreg.).

Flat-sheet microporous films can be sealed together, forming pouches that contain hydrophilic formulations and beneficial agents. The flat-sheet microporous film can also be sealed over the opening of an impermeable container. Alternatively, hollow fibers having microporous walls can be used with their ends sealed, enclosing the hydrophilic formulation and the beneficial agent within the lumen of the fiber.

Methods for using the devices of this invention include placing these devices in home, office, or other living space. Devices of this invention can also be used to deliver agents to such environments of use as backyards, greenhouses, or agricultural fields by placing devices in moist soil or in water. In such cases, the devices are placed into the soil or water such that the hydrophobic membrane is immersed and such that the delivery port for release of beneficial agent is in the air. Likewise, such devices could be used to deliver beneficial agent to air-supply systems, such as heating, cooling, oxygenation, or filtered air.

It should be understood that the invention is not limited to the particular embodiments shown and described herein, but that various changes and modifications may be made without departing from the spirit and scope of this novel concept as defined by the following claims.

EXAMPLE 1

Osmotic Water Flux Through Hydrophobic Microporous Films

Devices were made to measure the water flux through hydrophobic microporous films by sealing the films to one end of a length of polyethylene tubing. Polyethylene tubing (inner diameter of ½ inch) was cut to about 15 cm long and one end was heated by placing the tubing on end onto a hot plate. The tubing was heated until the polymer at the end of the tubing was visibly melted. The tubing was then removed from the hot plate and pressed onto the hydrophobic microporous films, bonding the films to the melted end of the tubing. The tubing with one end sealed by the hydrophobic film was filled to a level of about 9 cm with a saturated solution of sodium chloride with excess solids in water. To measure the water flux into these tubes through the hydrophobic films, the sealed tubes were placed in a water reservoir (beakers of water). The water level in the beaker was lower than the water level in the tubing so that any hydrostatic pressure would cause the solution in the tubing to go through the film at the bottom of the tube and into the water in the beaker if there were leaks in the tubing. Water flux was measured by weight gain on the sealed tube, and salt flux into the beaker of water was measured by measuring the conductivity of the water in the beaker. The tests were continued until the water level in the tubes rose to the top of the tubing and overflowed. The rising water level in the tubes confirmed that the water was entering the tubes through the hydrophobic microporous films by osmosis rather than by diffusion. Results from these tests are shown in Table I for several different films. The water-flux values were normalized to one square centimeter of surface area of hydrophobic microporous film. As shown in the table, all of the hydrophobic microporous films allowed osmotic imbibition of water and prevented any detectable flux of salt out into the water reservoir (no salt in the water reservoir is another indication that water was imbibed into the tubing by osmosis rather than by diffusion). Differences in porosity and thickness of the films led to corresponding differences in water flux.

TABLE I

Water Flux Through Hydrophobic Microporous Films Using Sodium Chloride As The Osmagent

| Material | Trade Name | Manufacturer | Location | Salt Flux (mg/ $cm^2$-day) | Water Flux (g/$cm^2$-day) |
|---|---|---|---|---|---|
| Polypropylene | Accurel PP type 2E | Akzo Nobel | Wuppertal, Germany | <0.01 | 1.1 |

TABLE I-continued

Water Flux Through Hydrophobic Microporous Films Using Sodium Chloride As The Osmagent

| Material | Trade Name | Manufacturer | Location | Salt Flux (mg/ $cm^2$-day) | Water Flux (g/$cm^2$-day) |
|---|---|---|---|---|---|
| Polypropylene | Celgard 4400 | Hoechst Celanese | Charlotte, NC | <0.01 | 0.3 |
| Polytetrafluoroethylene (PTFE) | Fluoropore ALPO9025 | Millipore | Bedford, MA | Not measured | 1.0 |
| PTFE | 3 µm | Millipore | Bedford, MA | <0.01 | 2.5 |
| PTFE | 0.5 µm | Millipore | Bedford, MA | <0.01 | 2.0 |
| PTFE | 1.2 µm | Sartorius | Bohemia, NY | <0.01 | 2.7 |
| PTFE | 5 µm | Sartorius | Bohemia, NY | <0.01 | 2.9 |
| High Density Polyethylene | MSX-4025 | 3M | Minneapolis, MN | <0.01 | 2.3 |

EXAMPLE 2

Osmotic Water Flux Through Hydrophobic Microporous Tubes

Devices were made to measure the osmotic water flux through hydrophobic microporous tubing. Porous polypropylene tubes (from Akzo, Nobel, Wuppertal, Germany) were obtained that had an inner diameter of 0.5 cm and outer diameter of 0.9 cm. The tubes were cut to about 15 cm in length and sealed at one end with a dense film of polytetrafluoroethylene (glued with hot-melt adhesive). The tubing was filled with a slurry of sodium chloride to a level of about 9 cm from the bottom (about 2 ml). To measure water flux, these tubes were placed into a water reservoir. The water in the reservoir was slightly less than 9 cm deep so that if there were leaks in the tubes, water would flow out of the tubes and into the water reservoir due to the difference in hydrostatic pressure. Water flux was measured by weight gain of the tubes. The tests were continued until the water level rose in the tubes to the top of the tubes and overflowed. The water flux normalized for surface area was 0.1 g/$cm^2$-day. The salt concentration in the water reservoir was also measured (by conductivity) to detect salt diffusing out of the tubes into the water reservoir. In all tests no salt was detected in the water reservoir, indicating that the water was imbibed into the tubes by osmosis through the pores in the hydrophobic microporous tubing material.)

EXAMPLE 3

Release Rates of Fragrance Dependent on the Osmotic Driving Force

Devices similar to those described in Example 1 were made to demonstrate osmotically driven release of a fragrance. Tubes were made that were sealed with porous polypropylene films (Accurel, PP type ZE, Akzo Nobel, Wuppertal, Germany). The tubes were filled with various slurries of osmagent as listed in Table II. On top of the water/osmagent slurries was placed a fragrance oil that was immiscible with the aqueous slurry. The top of the tube was sealed with an emanator pad (the emanator pad consisted of thick filter paper 2.1 cm in diameter) to spread the fragrance out, increasing the surface area and allowing the fragrance to evaporate into the air. The fragrance-containing tubes were placed into beakers of water to initiate release. Due to osmotic imbibition of water into the osmagent slurry, the fragrance was pumped to the emanator pad, where it evaporated into the air. The fragrance release rates were measured and are listed in Table II. As shown, the release rates are proportional to the osmotic driving force across the hydrophobic microporous film. Without an osmagent the release of fragrance was much lower, as expected for a device that is not osmotically pumping the fragrance to the emanator pad.

TABLE II

Release Rates of Fragrance Dependent on Osmagent

| Osmagent | Osmotic Driving Force (atm) | Fragrance Release Rate (mg/day) |
| --- | --- | --- |
| Sodium chloride | 280 | 802 |
| Sodium bicarbonate | 60 | 155 |
| Lactose | 19 | 40 |
| None (water only) | 0 | 0 |

EXAMPLE 4

Release Rates of Fragrance Dependent on the Surface Area of the Porous Hydrophobic Film Devices were made as described in Example 3 except that the tubing diameter was different. Devices were made that had inner diameters of either ½ or ¼ inch. The surface area of the hydrophobic microporous film attached to the end of the tubing was 0.8 $cm^2$ for the ½ inch tubing and 0.2 $cm^2$ for the ¼ inch tubing. In each of the devices a slurry of sodium chloride was used as the osmagent. The devices were placed in water and monitored to determine the release rate of the fragrance. Fragrance release rates were 801 mg/day for the device having 0.8 $cm^2$ of surface area and 160 mg/day for the device having 0.2 $cm^2$ of surface area. The release rate of fragrance was proportional to the surface area of the hydrophobic microporous film, indicating that the release of fragrance was controlled by the osmotic imbibition of water into the device, which then pumped the fragrance out to the emanator pad.

EXAMPLE 5

Release of Insect Pheromone From Osmotic Device Using a Porous Hydrophobic Film

Devices were made as described in Example 3 except that instead of loading the device with a fragrance oil, the devices were loaded with an insect pheromone (E-4-tridecenyl aetate) that is used to disrupt mating of the tomato pinworm. Two types of devices were made: one contained sodium chloride as the osmagent and the other did not contain an osmagent. The devices were placed in moist soil and the release rates measured. The release rate from the device containing sodium chloride as the osmagent was 720 mg/$cm^2$-day, whereas without an osmagent the release rate was less than 1 mg/$cm^2$-day. Thus, osmotic imbibition of water from the soil caused the pheromone to be pumped out at a rate much higher than was achieved without an osmotic device.

EXAMPLE 6

Osmotic Imbibition of Water from Air at 100% RH to Pump Fragrance from Device A

Devices were made as described in Example 3. The hydrophilic formulation (osmagent) used in these devices was a slurry of sodium chloride. The fragrance-containing dispensers were suspended in air maintained at 100% RH at room temperature. Osmotic imbibition of water from the air through the hydrophobic microporous membrane and into the hydrophilic formulation forced the fragrance oil to the top of the tube where it could be released. The water flux into these devices was measured to determine the rate of osmotic imbibition (this rate of osmotic imbibition could be translated to release of fragrance since imbibition of water results in equivalent volumes of fragrance pumped out of the device). The water flux into the devices was about 0.1 g/$cm^2$-day indicating that about 85 mg/day of fragrance could be delivered from a device having a membrane area of 1 $cm^2$ and placed in air at 100% RH.

We claim:

1. An osmotic device for the controlled release of a beneficial agent to a non-aqueous environment comprising:

a. a hydrophilic formulation comprising an osmagent;

b. a beneficial agent;

c. a container surrounding the hydrophilic formulation, the beneficial agent, and a water reservoir, said container having at least in part between the water reservoir and the hydrophilic formulation, a semipermeable hydrophobic microporous material having pores that have an average pore size between about 0.1 μm and 30 μm said pores substantially filled with a gas phase, said hydrophobic material permeable to water in the vapor phase and said hydrophobic material impermeable to liquid water at a pressure less than 100 Pa, said hydrophobic material having a contact angle with water greater than 50 degrees, and said container having at least one opening through which the beneficial agent is released from the device; and d. a water reservoir in a sealed compartment of the container that when the device is activated, the seal is disrupted allowing water vapor from the reservoir to be available for transport through the semipermeable material.

2. A method for the controlled deliver of a beneficial agent to a non-aqueous environment of use which comprises breaking a seal between a water reservoir and the semipermeable material and placing the device of claim 1 into the environment of use.

3. An osmotic device for the controlled release of a beneficial agent by osmotic pumping to a non-aqueous environment comprising:

a. a hydrophilic formulation comprising an osmagent;

b. a beneficial agent; and c. a container surrounding the hydrophilic formulation and the beneficial agent, said container at least in part a semipermeable hydrophobic microporous material having pores that have an average pore size between about 0.1 μm and 30 μm, said pores substantially filled with a gas phase, said hydrophobic material permeable to water in the vapor phase and said hydrophobic material impermeable to liquid water at a pressure less than 100 Pa, said hydrophobic material having a contact angle with water greater than 50 degrees, and said container having at least one opening through which the beneficial agent is released from the device;

wherein the semipermeable hydrophobic membrane has a water vapor transmission rate greater than 2 g-mm/$m^2$-24 hours, a void volume of between 5% and 95%, a thickness of between 5 μm and 2 cm, and wherein the semipermeable hydrophobic membrane in the nonporous state is substantially impermeable to the beneficial agent and has an intrinsic permeability to water of less than $1 \times 10^{-7}$ cm$^3$(STP)-cm/cm$^2$-sec-cmHg.

4. The osmotic device as recited in claim 3, wherein the hydrophilic formulation has a surface tension of about 60–75 dyn/cm.

5. The osmotic device as recited in claim 4 wherein the osmagent is a sugar.

6. The osmotic device as recited in claim 4 wherein the osmagent is a salt.

7. The osmotic device as recited in claim 4 wherein the hydrophilic formulation includes an aqueous swellable material.

8. The osmotic device as recited in claim 4 wherein said semipermeable hydrophobic material is selected from polyethylene, polypropylene, polyvinyl chloride, polytetrafluoroethylene, polystyrene, polycarbonate, polyethylene-terephthalate, polysulfones, polyacrylonitrile, polyvinylidene chloride, polyamides, polyimides, polyvinylidene fluoride, polyacrylic acid derivatives, natural waxes, or synthetic waxes.

9. The osmotic device as recited in claim 4 wherein said membrane material is polyethylene or polypropylene.

10. The osmotic device as recited in claim 4 wherein the surface area of said membrane material can be increased or decreased to effectively increase or decrease the release rate of beneficial agent.

11. An osmotic device for the controlled release of a beneficial agent by osmotic bursting to a non-aqueous environment comprising:
   a. a hydrophilic formulation comprising an osmagent;
   b. a beneficial agent; and
   c. a container surrounding the hydrophilic formulation and the beneficial agent, said container at least in part a semipermeable hydrophobic microporous material having pores that have an average pore size between about 0.1 µm and 30 µm, said pores substantially filled with a gas phase, said hydrophobic material permeable to water in the vapor phase and said hydrophobic material impermeable to liquid water at a pressure less than 100 Pa, said hydrophobic material having a contact angle with water greater than 50 degrees, and said container having at least one opening through which the beneficial agent is released from the device;
wherein the semipermeable hydrophobic membrane has a water vapor transmission rate greater than 2 g-mm/m$^2$-24 hours, a void volume of between 5% and 95%, a thickness of between 5 µm and 2 cm, and wherein the semipermeable hydrophobic membrane in the nonporous state is substantially impermeable to the beneficial agent and has an intrinsic permeability to water of less than $1 \times 10^{-7}$ cm$^3$(STP)-cm/cm$^2$-sec-cmHg.

12. The osmotic device as recited in claim 11 wherein said device is in the shape of a flower, bush, fern or other form resembling a plant.

13. The osmotic device as recited in claim 11, wherein the hydrophilic formulation has a surface tension of about 60–75 dyn/cm.

14. The osmotic device as recited in claim 13 wherein the osmagent is a sugar.

15. The osmotic device as recited in claim 13 wherein the osmagent is a salt.

16. The osmotic device as recited in claim 13 wherein the hydrophilic formulation includes an aqueous swellable material.

17. The osmotic device as recited in claim 13 wherein said semipermeable hydrophobic material is selected from polyethylene, polypropylene, polyvinyl chloride, polytetrafluoroethylene, polystyrene, polycarbonate, polyethylene-terephthalate, polysulfones, polyacrylonitrile, polyvinylidene chloride, polyamides, polyimides, polyvinylidene fluoride, polyacrylic acid derivatives, natural waxes or synthetic waxes.

18. The osmotic device as recited in claim 13 wherein said membrane material is polyethylene or polypropylene.

19. The osmotic device as recited in claim 13 wherein a the surface area of said membrane material can be increased or decreased to effectively increase or decrease the release rate of beneficial agent.

20. The osmotic device as recited in claim 3 wherein a movable piston component is placed between the hydrophilic formulation and the beneficial agent separating the two components.

21. The osmotic device as recited claim 11 wherein the beneficial agent is a fragrance, insecticide, herbicide, fungicide, pheromone, or food source.

22. The osmotic device as recited in claim 20, wherein the hydrophilic formulation has a surface tension of about 60–75 dyn/cm.

23. The osmotic device as recited in claim 22 wherein the osmagent is a sugar.

24. The osmotic device as recited in claim 22 wherein the osmagent is a salt.

25. The osmotic device as recited in claim 22 wherein the hydrophilic formulation includes an aqueous swellable material.

26. The osmotic device as recited in claim 22 wherein said semipermeable hydrophobic material is selected from polyethylene, polypropylene, polyvinyl chloride, polytetrafluoroethylene, polystyrene, polycarbonate, polyethylene-terephthalate, polysulfones, polyacrylonitrile, polyvinylidene chloride, polyamides, polyimides, polyvinylidene fluoride, polyacrylic acid derivatives, natural waxes or synthetic waxes.

27. The osmotic device as recited in claim 22 wherein said membrane material is polyethylene or polypropylene.

28. The osmotic device as recited in claim 22 wherein the surface area of said membrane material can be increased or decreased to effectively increase or decrease the release rate of beneficial agent.

29. The osmotic device as recited in claim 3 wherein a flexible layer is placed between the hydrophilic formulation and the beneficial agent separating the two components.

30. A method for the controlled delivery of a beneficial agent to a nonaqueous environment of use which comprises placing a portion of the device of claim 11 into an aqueous solution.

31. The osmotic device as recited in claim 29, wherein the hydrophilic formulation has a surface tension of about 60–75 dyn/cm.

32. The osmotic device as recited in claim 31 wherein the osmagent is a sugar.

33. The osmotic device as recited in claim 31 wherein the osmagent is a salt.

34. The osmotic device as recited in claim 31 wherein the hydrophilic formulation includes an aqueous swellable material.

35. The osmotic device as recited in claim 31 wherein said semipermeable hydrophobic material is selected from polyethylene, polypropylene, polyvinyl chloride, polytetrafluoroethylene, polystyrene, polycarbonate, polyethylene-terephthalate, polysulfones, polyacrylonitrile, polyvinylidene chloride, polyamides, polyimides, polyvinylidene fluoride, polyacrylic acid derivatives, natural waxes or synthetic waxes.

36. The osmotic device as recited in claim 31 wherein said membrane material is polyethylene or polypropylene.

37. The osmotic device as recited in claim 31 wherein the surface said membrane material can be increased or decreased to effectively increase or decrease the release rate of beneficial agent.

38. The osmotic device as recited in claim 3 wherein said device is in the shape of a flower, bush, fern or other form resembling a plant.

39. The osmotic device as recited in claim 3 wherein the beneficial agent is a fragrance, insecticide, herbicide, fungicide pheromone, or food source.

40. A method for the controlled delivery of a beneficial agent to a nonaqueous environment of use which comprises placing a portion of the device of claim 3 into an aqueous solution.

41. A method for the controlled delivery of a beneficial agent to a nonaqueous environment of use which comprises the device of claim 3 such that the hydrophobic microporous material is exposed to humid air.

42. A method for the controlled delivery of a beneficial agent to a nonaqueous environment of use which comprises the device of claim 11 such that the hydrophobic microporous material is exposed to humid air.

* * * * *